Feb. 27, 1973 C. G. KLEHM Plant Pat. 3,312
IRIS PLANT
Filed June 23, 1971
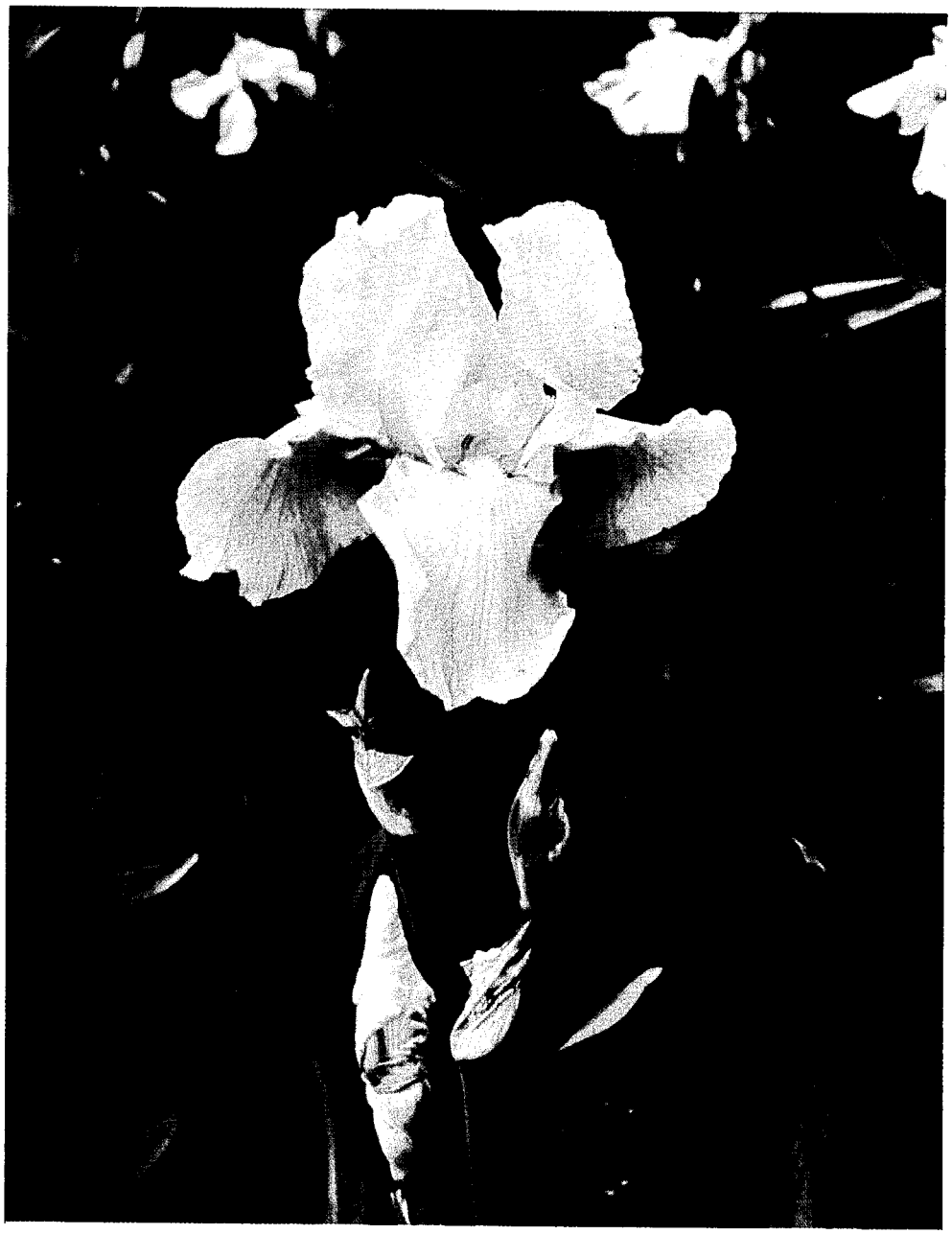
Inventor
Carl G. Klehm
By: Robb & Robb
Attorneys.

United States Patent Office

Plant Pat. 3,312
Patented Feb. 27, 1973

3,312
IRIS PLANT

Carl G. Klehm, 2 E. Algonquin Road,
Arlington Heights, Ill. 60005

Filed June 23, 1971, Ser. No. 156,139
Int. Cl. A01h 5/00
U.S. Cl. Plt.—68 1 Claim The present invention relates to a new and distinct variety of iris plant which was originated by crossing the iris variety known as "Blue Blazes" (unpatented) with the iris variety known as "Blue Giant" (unpatented), the former being the male parent and the latter being the female parent.

As the result of this breeding, I have selected and developed a new and improved iris variety as evidenced by the following unique combination of characteristics which are outstanding therein and which distinguish it from its parents, as well as from all other iris varieties of which I am aware:

(1) A vigorous habit of growth, with large rhizomes and strong, stiff stems;

(2) Distinctive rippled foliage;

(3) Extremely large flowers, with little or no crinkling or rippling anywhere on the blossoms;

(4) Outstanding "plasticity" of the flowers (flower falls hold a horizontal position during weathering) which contributes to their massive appearance; and (5) A distinctive and attractive pure white flower color, with bright golden beards on the flower falls.

Asexual reproduction of my new iris variety by division, as performed by me or under my direction and control at Arlington Heights, Barrington and Woodstock, Ill., shows that the foregoing characteristics and distinctions come true to form and are established and transmitted through succeeding propagations.

The accompanying drawing shows typical specimens of the vegetative growth and flowers of the new variety, as depicted in color as nearly true as it is reasonably possible to make the same in a color illustration of this character.

The following is a detailed description of my new iris variety, with color terminology in accordance with the Horticultural Colour Chart, published by the Royal Horticultural Society (1966), of London, England, except where general color terms of ordinary dictionary significance are obvious:

Locally where grown and observed: Arlington Heights and Barrington, Ill.

Parentage:

*Male parent.*—"Blue Blazes."

*Female parent.*—"Blue Giant."

Propagation: Holds its distinguishing characteristics through succeeding propagations by division.

*Plant*

Growth habit: Vigorous and robust.

Blooming habit: Annual; mid-season.

Stems: Tall (about 36 inches); stiff; strong.

Foliage: Rippled on top half of many leaves.

*Length.*—From about 26 inches to 28 inches.

*Breadth.*—About 2¼ inches.

*Quantity.*—Average.

*Color.*—Usually near Chrysocolla Green, Color No. 56/1.

Corms: Vigorous. Size—large.

*Flower*

Spike: Well-branched; from 3 to 6 flowers per spike.

Bud:

*Size.*—About 1½ inches long when color first shows.

*Color.*—Pure white.

*Opening habit.*—Expands to about 4½ inches before unfolding.

Open flower:

*Arrangement.*—Classical.

*Form.*—Broader than tall due to horizontal fall arrangement.

*Size.*—Extremely large; petals and falls range from about 4½ inches to 5 inches from claw to tip.

*Fragrance.*—Mild. Nature—typical iris.

*Keeping quality.*—Average.

Petals: Falls are of horizontal flaring form, with a high degree of "plasticity" (weather resistance).

*Shape.*—Standards are broadly arching.

*Color.*—Pure white.

*Reproductive organs*

Filaments: Usually 3; about 1¾ inches long.

Anthers: About ½ inch long. Color—pale yellow.

Pollen: Slightly fertile. Color—creamy white.

Pistils: 3 style arms. Color—pure white.

I claim:

1. A new and distinct variety of iris plant, substantially as herein shown and described, characterized particularly as to novelty by the unique combination of a vigorous habit of growth, with large rhizomes and strong, stiff stems, distinctive rippled foliage, extremely large flowers, with little or no crinkling or rippling anywhere on the blossoms, outstanding "plasticity" of the flowers (flower falls hold a horizontal position during weathering) which contributes to their massive appearance, and a distinctive and attractive pure white flower color, with bright golden beards on the flower falls.

No references cited.

ROBERT E. BAGWILL, Primary Examiner